(12) United States Patent
Onishi et al.

(10) Patent No.: US 9,719,942 B2
(45) Date of Patent: Aug. 1, 2017

(54) SINTERED CERAMIC AND CERAMIC SPHERE

(75) Inventors: Hiroshi Onishi, Osaka (JP); Hiroshi Ikeda, Osaka (JP); Hiroki Takimoto, Osaka (JP); Hiroshi Uemura, Osaka (JP); Kenji Yamada, Nara (JP); Hideki Ono, Nara (JP); Hiroyuki Matsuyama, Nara (JP)

(73) Assignees: NIKKATO CORPORATION, Osaka (JP); TSUBAKI NAKASHIMA CO., LTD., Nara (JP)

( * ) Notice: Subject to any disclaimer, the term of this patent is extended or adjusted under 35 U.S.C. 154(b) by 738 days.

(21) Appl. No.: 13/520,956

(22) PCT Filed: Nov. 11, 2010

(86) PCT No.: PCT/JP2010/070083
§ 371 (c)(1),
(2), (4) Date: Jul. 6, 2012

(87) PCT Pub. No.: WO2011/083624
PCT Pub. Date: Jul. 14, 2011

(65) Prior Publication Data
US 2012/0274941 A1    Nov. 1, 2012

(30) Foreign Application Priority Data

Jan. 7, 2010   (JP) ................... 2010-001660
Aug. 9, 2010   (JP) ................... 2010-178772

(51) Int. Cl.
G01N 21/00   (2006.01)
D06N 7/04    (2006.01)
(Continued)

(52) U.S. Cl.
CPC ......... G01N 21/95 (2013.01); C04B 35/584 (2013.01); C04B 35/638 (2013.01);
(Continued)

(58) Field of Classification Search
CPC .... C04B 2235/3217; C04B 2235/3873; C04B 2235/3878; C04B 2235/5409;
(Continued)

(56) References Cited

U.S. PATENT DOCUMENTS 5,187,127 A *  2/1993  Goto ............... C04B 35/584
                                              501/92
5,457,326 A   10/1995  Tsujita et al.
(Continued)

FOREIGN PATENT DOCUMENTS

EP    1 669 335 A1    6/2006
JP    06-329472 A    11/1994
(Continued)

OTHER PUBLICATIONS

International Search Report for PCT/JP2010/070083, mailing date of Jan. 25, 2011.

*Primary Examiner* — Sunghee Y Gray
(74) *Attorney, Agent, or Firm* — Westerman, Hattori, Daniels & Adrian, LLP

(57) ABSTRACT

Provided are a sintered ceramic and a ceramic sphere which are inhibited from suffering surface peeling due to fatigue resulting from repetitions of loading and can attain an improvement in dimensional accuracy when subjected to surface processing and which have excellent wear resistance and durability.

3 Claims, 14 Drawing Sheets

(51) Int. Cl.
*B32B 5/16* (2006.01)
*G01N 21/95* (2006.01)
*C04B 35/584* (2006.01)
*C04B 35/638* (2006.01)
*C04B 35/645* (2006.01)
*F16C 33/32* (2006.01)
*G01N 33/38* (2006.01)
*G01N 21/55* (2014.01)
*G01N 21/47* (2006.01)

(52) U.S. Cl.
CPC ......... *C04B 35/6455* (2013.01); *F16C 33/32* (2013.01); *G01N 21/55* (2013.01); *G01N 21/951* (2013.01); *G01N 33/388* (2013.01); C04B 2235/3217 (2013.01); C04B 2235/3225 (2013.01); C04B 2235/3873 (2013.01); C04B 2235/3878 (2013.01); C04B 2235/5409 (2013.01); C04B 2235/604 (2013.01); C04B 2235/6581 (2013.01); C04B 2235/661 (2013.01); C04B 2235/72 (2013.01); C04B 2235/77 (2013.01); C04B 2235/786 (2013.01); C04B 2235/94 (2013.01); C04B 2235/96 (2013.01); C04B 2235/963 (2013.01); F16C 2206/60 (2013.01); F16C 2220/20 (2013.01); G01N 2021/4735 (2013.01); G01N 2201/06113 (2013.01); Y10T 428/24413 (2015.01); Y10T 428/2982 (2015.01)

(58) Field of Classification Search
CPC ........ C04B 2235/604; C04B 2235/661; C04B 2235/72; C04B 2235/786; C04B 2235/94; C04B 2235/96; C04B 2235/963; C04B 35/584
USPC ................ 356/237.2, 445; 428/148, 402
See application file for complete search history.

(56) References Cited

U.S. PATENT DOCUMENTS

| | | |
|---|---|---|
| 5,612,265 A | 3/1997 | Bullock et al. |
| 2004/0191535 A1 | 9/2004 | Komatsu |
| 2006/0138717 A1 | 6/2006 | Wotting et al. |
| 2007/0197368 A1* | 8/2007 | Tsukuma ............. A61C 7/14 501/103 |
| 2008/0050005 A1 | 2/2008 | Nagashio |
| 2008/0081103 A1* | 4/2008 | Tauch ............... A61K 6/0276 427/2.29 |
| 2008/0167174 A1* | 7/2008 | Osthols ............. C04B 35/597 501/98.1 |
| 2008/0188369 A1* | 8/2008 | Osthols ............. C04B 35/597 501/87 |
| 2008/0303181 A1* | 12/2008 | Holand ............... A61C 5/10 264/16 |
| 2009/0224399 A1* | 9/2009 | Kaga ............... C04B 35/5935 257/712 |
| 2010/0054652 A1 | 3/2010 | Takao et al. |

FOREIGN PATENT DOCUMENTS

| | | | |
|---|---|---|---|
| JP | 06329472 | † 11/1994 | |
| JP | 08-247956 A | 9/1996 | |
| JP | 10279365 | † 10/1998 | |
| JP | 2000-185976 A | 7/2000 | |
| JP | 2000-319071 A | 11/2000 | |
| JP | 2000319071 | * 11/2000 | ............. G01N 21/55 |
| JP | 2001-122667 A | 5/2001 | |
| JP | 2001-172085 A | 6/2001 | |
| JP | 2001-261446 A | 9/2001 | |
| JP | 2002-326875 A | 11/2002 | |
| JP | 2002326875 | † 11/2002 | |
| JP | 2003-34581 A | 2/2003 | |
| JP | 2003-322154 A | 11/2003 | |
| JP | 2004161605 | † 6/2004 | |
| JP | 2008-051619 A | 3/2008 | |
| JP | 2008-273829 A | 11/2008 | |
| JP | 2010-127621 A | 6/2010 | |
| WO | 2008/111307 A1 | 9/2008 | |

\* cited by examiner
† cited by third party

| | SAMPLE No. | Al₂O₃+Y₂O₃ (wt%) | Al₂O₃ (wt%) | Y₂O₃ (wt%) | MOLDING POWDER SPECIFIC SURFACE AREA (m²/g) | SINTERING TEMPERATURE (°C) |
|---|---|---|---|---|---|---|
| EXAMPLE | 1 | 10 | 4 | 5 | 13 | 1750 |
| | 2 | 12 | 6 | 6 | 11 | 1650 |
| | 3 | 11 | 5 | 6 | 12 | 1780 |
| | 4 | 11 | 6 | 5 | 10 | 1720 |
| | 5 | 10 | 6 | 4 | 12 | 1750 |
| | 6 | 8 | 3 | 5 | 10 | 1600 |
| COMPARATIVE EXAMPLE | 1 | 12 | 4 | 8 | 13 | 1750 |
| | 2 | 5 | 3 | 2 | 12 | 1650 |
| | 3 | 7 | 2 | 5 | 8 | 1680 |
| | 4 | 13 | 6 | 7 | 10 | 1730 |
| | 5 | 8 | 4 | 4 | 11 | 1560 |
| | 6 | 9 | 5 | 4 | 12 | 1880 |
| | 7 | 11 | 6 | 5 | 11 | 1700 |
| | 8 | 10 | 5 | 5 | 17 | 1720 |
| | 9 | 10 | 4 | 6 | 12 | 1750 |

| | SAMPLE No. | BULK DENSITY (g/cm³) | AVERAGE GRAIN SIZE (μm) | FLAW SIZE (μm) | SNOW FLAKE (μm) | WEAR RESISTANCE /DURABILITY (m) |
|---|---|---|---|---|---|---|
| EXAMPLE | 1 | 3.23 | 1.8 | 0 | ≤10 | 1300.0 |
| | 2 | 3.19 | 1.4 | 7 | ≤10 | 1300.0 |
| | 3 | 3.22 | 1.8 | 0 | ≤10 | 1300.0 |
| | 4 | 3.20 | 1.5 | 3 | ≤10 | 1300.0 |
| | 5 | 3.21 | 1.5 | 0 | ≤10 | 1300.0 |
| | 6 | 3.18 | 1.4 | 0 | ≤10 | 1300.0 |
| COMPARATIVE EXAMPLE | 1 | 3.20 | 1.8 | 6 | 45 | 71.4 |
| | 2 | 3.02 | 1.2 | 23 | 27 | 422.3 |
| | 3 | 3.08 | 1.3 | 60 | 23 | 71.5 |
| | 4 | 3.22 | 1.5 | 7 | 35 | 301.8 |
| | 5 | 2.98 | * | ** | * | *** |
| | 6 | 3.16 | 3.5 | 55 | 47 | 21.5 |
| | 7 | 3.10 | 1.3 | 40 | ≤10 | 549.0 |
| | 8 | 3.21 | 1.6 | 15 | 18 | 647.0 |
| | 9 | 3.21 | 1.6 | 20 | 36 | 226.0 |

\* MEASUREMENT IS NOT POSSIBLE BECAUSE OF MULTIPLE AIR HOLES

\*\* MULTIPLE AIR HOLES OF 10 μm OR MORE ARE INCLUDED

\*\*\* MEASUREMENT IS NOT PERFORMED BECAUSE OF MULTIPLE FLAWS

| SILICON NITRIDE SPHERE | AGAINST SUJ-2 CRUSHING VALUE (kN) | DESTRUCTION TARGET SIDE | TWO-SPHERE CRUSHING VALUE (kN) |
|---|---|---|---|
| COMPARATIVE EXAMPLE 4 | 67.7 | SUJ-2 | 22.7 |
| | 96.1 | SUJ-2 | 23.5 |
| | 78.5 | SUJ-2 | 21.6 |
| | 117.7 | SUJ-2 | 20.6 |
| | 82.4 | SUJ-2 | 19.6 |
| | 115.7 | SUJ-2 | 20.6 |
| COMPARATIVE EXAMPLE 6 | 78.5 | SUJ-2 | 19.2 |
| | 107.9 | SILICON NITRIDE | 16.2 |
| | 112.8 | SUJ-2 | 15.0 |
| | 107.9 | SUJ-2 | 14.3 |
| | 78.5 | SUJ-2 | 13.7 |
| | 109.8 | SILICON NITRIDE | 14.7 |
| EXAMPLE 5 | 101.0 | SUJ-2 | 21.2 |
| | 103.0 | SUJ-2 | 20.5 |
| | 113.8 | SUJ-2 | 24.8 |
| | 107.9 | SUJ-2 | 22.9 |
| | 120.6 | SUJ-2 | 21.6 |

* SAME MANUFACTURING NUMBER IS USED FOR ALL SUJ-2 BALLS

Fig. 7

| SAMPLE | SPHERICITY | | SURFACE ROUGHNESS (Rmax) | |
|---|---|---|---|---|
| | COMPARATIVE EXAMPLE 4 | EXAMPLE 5 | COMPARATIVE EXAMPLE 4 | EXAMPLE 5 |
| 1 | 0.03 | 0.03 | 0.0068 | 0.0045 |
| 2 | 0.02 | 0.03 | 0.0127 | 0.0049 |
| 3 | 0.03 | 0.03 | 0.0083 | 0.0061 |
| 4 | 0.03 | 0.03 | 0.0067 | 0.0053 |
| 5 | 0.03 | 0.04 | 0.0069 | 0.004 |
| 6 | 0.02 | 0.03 | 0.0089 | 0.0061 |
| 7 | 0.02 | 0.02 | 0.0071 | 0.0077 |
| 8 | 0.03 | 0.03 | 0.0078 | 0.0065 |
| 9 | 0.03 | 0.03 | 0.0065 | 0.0047 |
| 10 | 0.02 | 0.04 | 0.0053 | 0.0054 |

UNIT IS μm

Fig. 8

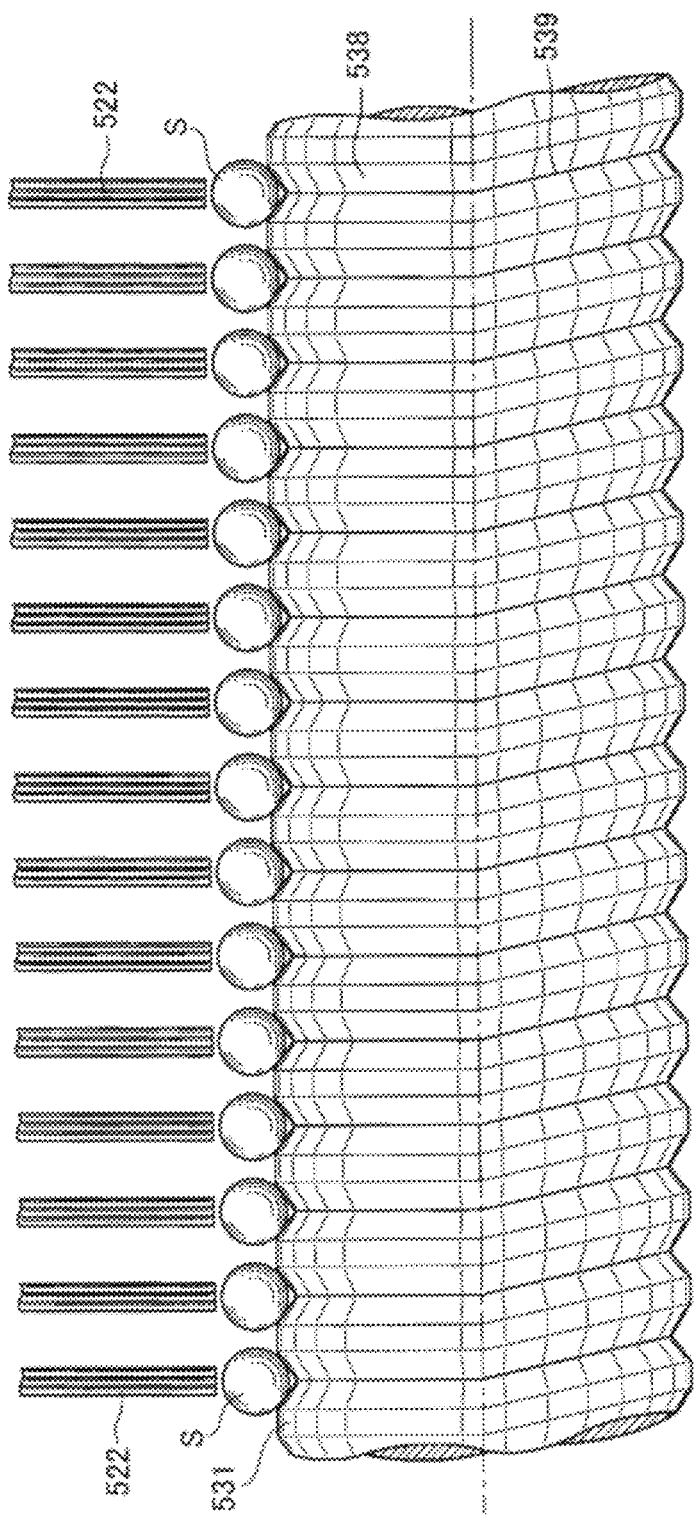

SINTERED CERAMIC AND CERAMIC SPHERE

TECHNICAL FIELD

The present invention relates to a sintered ceramic, a ceramic sphere and a ceramic-sphere inspection device which have excellent wear resistance and durability, and, more particularly, relates to a sintered ceramic and a ceramic sphere which are suitable to apply to a rolling member used in a sliding device such as a spherical, columnar, circular truncated conical, barrel-shaped or hourglass bearing or a ball nut, or a valve body and the like of a fluidic valve which controls a high pressure fluid, and a ceramic-sphere inspection device which is suitable to inspect a state of an inner part of a surface layer of this ceramic sphere.

BACKGROUND ART

Although a sintered ceramic requires higher manufacturing cost than metal such as steel, it has high mechanical strength and excellent wear resistance and rigidity, has a lighter specific weight than steel and has an insulating property and high corrosion resistance.

By utilizing these characteristics, and being used as a wear resistant member for a sliding device such as a bearing or a ball nut, or a valve and the like of a fluidic valve which controls a high pressure fluid, it is possible to reduce the weight, prevent damages due to a load and repetitions of sliding or damages such as wear, corrosion and electrical corrosion, maintain performance for a long period of time, increase the life of components and reduce maintenance labor.

For bearings and the like which are used in an environment particularly in the vicinity of wind power generators, compressors of air-conditioners, vehicles and the like of electrical vehicles and hybrid vehicles and electrical systems, and in which the temperature and humidity significantly change, ceramic spheres are frequently employed instead of metals such as steel which is significantly influenced by damages and the like by corrosion or electric corrosion and requires lower manufacturing cost, since the ceramic spheres require lower maintenance cost than metals such as steel.

Further, a rigid, light weight and long-life valve body is required for a fluidic valve in particular which is opened and closed at a high speed under a high pressure, and therefore employing a ceramic sphere for the valve body brings a significant advantage.

A general ceramic is sintered using a plurality of raw materials and sintering agents and, when, for example, a silicon nitride sintered compact is sintered, silicon nitride ($Si_3N_4$) which is a raw material hardly causes solid-state sintering itself and cannot provide a dense sintered compact, and therefore a rare-earth oxide such as $Y_2O_3$ and an oxide such as $Al_2O_3$ are mixed and molded as sintering agents and are densified by liquid-phase sintering to obtain a silicon nitride sintered compact.

Thus, when a ceramic is sintered using a plurality of raw materials and sintering agents, fine flaws are produced on a surface or in an inner part depending on conditions and these flaws cause surface peeling due to fatigue resulting from repetitions of loading.

For example, known Patent Literature 1 discloses defining the porosity of a sintered compact and the maximum air hole diameter in a grain boundary phase, and obtaining a wear resistant member made of a silicon nitride sintered compact which has an excellent rolling life because flaws such as scratches and cracks on a rolling element surface lead to deterioration of reliability of quality.

However, the technique disclosed in Patent Literature 1 only targets at flaws such as scratches, the cracks and the air holes, and does not provide any countermeasure for white spots (snow flakes) which influence more on wear resistance and durability than on the scratches, cracks and air holes.

Further, known Patent Literature 2 discloses focusing on the composition which is observed as white branches formed with an aggregate of micropores (fine air holes corresponding to fine flaws) in a range of from a surface to the depth of 1 mm, and, if the aggregate of the micropores has a given size or less, causing peeling due to rolling fatigue which causes a trouble when a ball is used for a bearing material, irrespective of the rate of an area which occupies in the entire area of the ball.

However, although the aggregate of micropores has a small size, if the amount of micropores is great, a crushing load decreases, thereby causing damages and causing surface peeling due to fatigue resulting from repetitions of loading.

Further, this white branch portion has different characteristics such as the rigidity and the density from other portions, and therefore, even a small white branch portion blocks improvement in dimensional accuracy such as the sphericity and the surface roughness when a silicon nitride sphere or a silicon nitride roller which is a wear resistant member is polished and processed, resulting in causing surface peeling due to fatigue resulting from repetitions of loading.

Furthermore, there are problems that flaws or remaining internal distortion inside a silicon nitride sphere or a silicon nitride roller which is a wear resistant member make an internal stress state uneven and become starting points of destruction, or cause wear or vibration because dimensional accuracy does not improve as described above.

Still further, when a ceramic sphere is inspected as a product, a means is required for observing and inspecting that there are no flaws such as scratches, cracks and air holes near a surface nor snow flakes without destroying the ceramic sphere.

As a device which inspects a ceramic sphere without destroying the ceramic sphere, a device which optically observes the surface of the ceramic sphere as disclosed in, for example, Patent Literature 3 and a device which observes the surface of the ceramic sphere and the inner part of the surface layer by means of an ultrasonic wave as disclosed in Patent Literature 4 are known.

CITATION LIST

Patent Literature

Patent Literature 1: Japanese Patent Application Laid-Open (JP-A) No. 2002-326875 (all pages and FIG. 2)

Patent Literature 2: JP-A No. 6-329472 (all pages and FIG. 1)

Patent Literature 3: JP-A No. 2008-51619 (all pages and FIGS. 1 and 3)

Patent Literature 4: JP-A No. 2010-127621 (all pages and FIG. 2)

SUMMARY OF INVENTION

Technical Problem

As a result of a devoted study in light of the above current situation, the inventors found that it is possible to obtain a sintered ceramic which has excellent wear resistance and durability and solves the above problem, by limiting the composition of sintering agents, adjusting the bulk density and the average grain size in a given range, controlling the composition from the surface to a given depth and manufacturing the sintered ceramic under limited conditions.

The conventional techniques are supposed to deal with flaws such as scratches, cracks and air holes which cause peeling due to rolling fatigue as disclosed in the above Patent Literatures.

However, as a result of the devoted study, the inventors found that only reducing these flaws as much as possible is not sufficient for improvement in wear resistance and durability.

That is, the inventors found that, although these flaws can be observed by a scanning electron microscope (SEM), other flaws cannot be observed by the SEM, and the presence of white spots (snow flakes) which is observed by an optical microscope significantly influences wear resistance and durability.

While these snow flakes are not observed at all by the SEM observation as illustrated in FIG. 2, the snow flakes are clearly observed by the optical microscope.

These snow flakes are not observed by the SEM observation, are not white branches made of an aggregate of micropores as disclosed in Patent Literature 2 and are supposed to have a slight difference in the composition of the crystal grain boundary phase from other portions, and this slight difference in the composition significantly influences wear resistance and durability.

Further, the inventors found that, when a sintered ceramic is used for a wear resistant member, not only flaws such as scratches, cracks and air holes on the surface of the member and near the surface, but also snow flakes significantly influence wear resistance and durability and therefore whether or not there are the flaws and the snow flakes on the surface and near the surface matters, and it is possible to provide the composition without the flaws and the snow flakes from the surface to the depth of 250 µm by limiting the composition of a sintering agent, adjusting the bulk density and the average grain size in a given range and manufacturing the sintered ceramic under limited conditions.

It is therefore an object of the present invention to provide a sintered ceramic and a ceramic sphere which can reduce surface peeling due to fatigue resulting from repetitions of loading and attain improvement in dimensional accuracy upon process of the surface, and has excellent wear resistance and durability.

Further, when the ceramic sphere is inspected as a product taking into account characteristics found by the inventors, a means is required for observing and inspecting that there are not defects such as scratches, cracks and air holes near the surface nor snow flakes without destroying the ceramic sphere.

However, although a device which performs optical observation as in the above Patent Literature 3 detects light reflected from the surface and therefore can detect flaws appeared on the surface and a difference in the color tone such as snow flakes, this device has had a problem that the device cannot observe flaws, snow flakes and the like in the inner part of the surface layer which do not appear on the surface.

Further, although a device which performs observation using an ultrasonic wave as in Patent Literature 4 can detect, for example, scratches, cracks and air holes of varying reflections of ultrasonic waves in the inner part of the surface layer, the device has difficulty in detecting snow flakes formed based on the above slight difference in the composition of the crystal grain boundary phase, based on reflections of ultrasonic wave.

It is therefore another object of the present invention to provide a ceramic-sphere inspection device which detects whether or not there are flaws and snow flakes in the inner part of the surface layer without destroying a ceramic sphere with a simple configuration.

Solution to Problem

To solve the above problem, the invention according to a first aspect provides a sintered ceramic which is obtained by molding and sintering a mixture including silicon nitride and a sintering agent made of Al2O3 and Y2O3, wherein a bulk density is 3.1 g/cm3 or more, an average grain size is 3 mm or less, and there are no flaw of 10 mm or more from a surface to a depth of 250 mm and no white spot (snow flake) of 20 mm or more.

To solve the above problem, the invention according to a second aspect provides a ceramic sphere which is obtained by molding and sintering in a spherical shape a mixture including silicon nitride and a sintering agent made of Al2O3 and Y2O3, wherein a bulk density is 3.1 g/cm3 or more, an average grain size is 3 mm or less, and there are no flaw of 10 mm or more from a surface to a depth of 250 mm and no white spot (snow flake) of 20 mm or more.

To solve the above problem, the invention according to a third aspect provides a wear resistant member formed using a sintered ceramic, wherein a surface of the sintered ceramic according to the first aspect is processed to make a rolling bearing member.

To solve the above problem, the invention according to a fourth aspect provides a ceramic-sphere inspection device including a rotation supporter which rotatably supports the ceramic sphere according to the second aspect, at a given position, a light projector which emits illuminating light toward a surface of the ceramic sphere, a light receiver which detects light reflected from the ceramic sphere as inspection light, and a processor which evaluates a state of an inner part of a surface layer of the ceramic sphere in response to a detection output from the light receiver, wherein the light receiver does not detect the illuminating light emitted from the light projector and reflected at the surface of the ceramic sphere.

To solve the above problem, the invention according to a fifth aspect provides the ceramic-sphere inspection device with further configurations according to the fourth aspect, wherein the light projector includes a light source, and a light projecting unit which guides light of the light source to the surface of the ceramic sphere as illuminating light, the light receiver includes a light amount detecting unit, and a light receiving unit which guides the inspection light from the ceramic sphere to the light amount detecting unit, and at least one of the light projecting unit and the light receiving unit includes at a front end a contact surface which can contact the surface of the ceramic sphere.

To solve the above problem, the invention according to a sixth aspect provides the ceramic-sphere inspection device with further configurations according to the fourth or fifth aspects, wherein a plurality of light receiving units are provided over a semicircle of an outer peripheral circle in a cross section passing a center of the ceramic sphere, and the rotation supporter rotates the ceramic sphere at a right angle with respect to the outer peripheral circle on which the light receiving units are provided.

To solve the above problem, the invention according to a seventh aspect provides the ceramic-sphere inspection device with further configurations according to the fourth or fifth aspects, wherein a plurality of light receiving units are provided along part of an outer peripheral circle in a cross section passing a center of the ceramic sphere and the rotation supporter rotates the ceramic sphere at a right angle with respect to the outer peripheral circle on which the light receiving units are provided, and rotates the ceramic sphere in an outer peripheral circle direction on which the light receiving units are provided such that the ceramic sphere is shifted by a width of the plurality of light receiving units when finishing rotating round.

To solve the above problem, the invention according to an eighth aspect provides the ceramic-sphere inspection device with further configurations according to the fourth or fifth aspects, wherein only one light receiving unit is provided, and the rotation supporter rotates the ceramic sphere in a given direction, and slightly rotates the ceramic sphere at a right angle with respect to a rotation direction.

To solve the above problem, the invention according to a ninth aspect provides the ceramic-sphere inspection device with further configurations according to one of the sixth through eighth aspects, wherein a same number of light projecting unit as the number of the plurality of light receiving units is provided, and each one of the light projecting units is provided adjacent to each of the plurality of light receiving units.

To solve the above problem, the invention according to a tenth aspect provides the ceramic-sphere inspection device with further configurations according to one of the fifth through ninth aspects, wherein the rotation supporter can be intermittently driven, at least one of the light projecting unit and the light receiving unit can proceed and retreat to and from a surface direction of the ceramic sphere, and a contact surface at a front end of at least one of the light projecting unit and the light receiving unit closely attaches to the surface of the ceramic sphere when driving of the rotation supporter is stopped, and is detached from the surface of the ceramic sphere when the rotation supporter is driven.

Advantageous Effects of Invention

The sintered ceramic of the invention according to the first aspect and the ceramic sphere of the invention according to the second aspect can attain improvement in wear resistance and dimensional accuracy without fine flaws and remaining internal distortion and without causing surface peeling due to fatigue resulting from repetitions of loading and making an uneven internal stress state and a starting point of destruction.

The wear resistant member of the invention according to the third aspect can improve durability of a rolling bearing, and reduce wear and vibration.

With the ceramic-sphere inspection device of the invention according to the fourth aspect, the light receiver does not detect illuminating light emitted from the light projector and reflected at the surface of the ceramic sphere, and can detect as inspection light only illuminating light transmitted and diffused in the inner part of the surface layer of the ceramic sphere and reflected from the inner part, so that it is possible to accurately detect whether or not there are flaws in the inner part of the surface layer and snow flakes formed based on a slight difference in the composition of the crystal grain boundary phase without destroying the ceramic sphere and without depending on the surface state.

Further, the optical transmittance is determined according to a material and sintering conditions of the ceramic sphere, so that it is possible to inspect whether or not the material of the ceramic sphere is good and the ceramic sphere is sintered well by observing the total amount of inspection light detected at a plurality of portions.

With the configuration according to the fifth aspect, at least one of the light projecting unit and the light receiving unit has at the front end the contact surface which can contact the surface of the ceramic sphere, so that it is possible to reliably prevent illuminating light emitted from the light projecting unit and reflected at the surface of the ceramic sphere from being detected by the light receiving unit even when the light projecting unit and the light receiving unit are close.

With the configuration according to the sixth aspect, it is possible to observe the entire surface of the ceramic sphere and efficiently inspect the ceramic sphere only by rotating the ceramic sphere once.

With the configuration according to the seventh aspect, it is possible to reduce the number of light projecting units and the number of light receiving units, simplify the entire device and reduce cost.

With the configuration according to the eighth aspect, it is possible to reduce the number of light projecting units and the number of light receiving units to one respectively, further simplify the entire device, reduce cost, and the light amount and sensitivity of a plurality of light projecting units and light receiving units do not need to be adjusted at all and, consequently, it is easy to maintain inspection accuracy.

With the configuration according to the ninth aspect, for example, the detection sensitivity does not need to be adjusted based on the relationship between positions of the light projecting unit and the light receiving unit and, consequently, it is easy to maintain inspection accuracy.

With the configuration according to the tenth aspect, the contact surface at the front end of at least one of the light projecting unit and the light receiving unit is not damaged or worn away due to sliding against the surface of the ceramic sphere and, consequently, it is easy to maintain inspection accuracy.

BRIEF DESCRIPTION OF DRAWINGS

FIG. 5 illustrates sintering conditions of sintered ceramics according to the present invention and comparative examples.

FIG. 6 illustrates endurance test results of a bearing ball made of a ceramic sphere according to the present invention and the comparative examples.

FIG. 7 illustrates two-sphere crushing load test results of a bearing of a 3/8 inch standard according to the present invention and comparative examples.

FIG. 8 illustrates two-sphere crushing load test results of a bearing ball of a 5/32 inch standard according to the present invention and the comparative examples.

FIG. 16 is a schematic view of a still another embodiment of the ceramic-sphere inspection device according to the present invention.

DESCRIPTION OF EMBODIMENTS

Hereinafter, each requirement which need to be satisfied by a sintered ceramic according to the present invention which has excellent wear resistance will be described in detail.

The sintered ceramic according to the present invention needs to have the bulk density of 3.1 g/cm$^3$ or more and, preferably, have the bulk density of 3.2 g/cm$^3$ or more.

When the bulk density is less than 3.1 g/cm$^3$, there are multiple micropores inside the sintered compact, and therefore resistance against the external stress such as wear and shock deteriorates, and wear resistance and durability decrease.

Further, the average grain size needs to be 3 μm or less and, more preferably, is 2 μm or less.

When the average grain size exceeds 3 μm, the average grain size increases and the crystal grain boundary phase area increases, and, when snow flakes are formed in this crystal grain boundary, the flaw size increases and remaining internal distortion becomes significant, thereby causing significant decrease in wear resistance and durability.

In addition, the average crystal grain size in the sintered ceramic according to the present invention is measured by mirror-finishing the surface of the sintered compact using a diamond wheel and abrasive grains and applying HF etching or plasma etching to the surface, and is observed by a SEM at the magnification at which 100 or more average grain sizes can be observed in one field of view.

Silicon nitride crystal grains of the sintered ceramic according to the present invention are mainly columnar, and therefore, a long diameter and a short diameter of the crystal grains are measured to obtain the grain diameter of one crystal grain based on grain diameter=(long diameter+short diameter)/2.

Grain diameters of 100 crystal grains are obtained in this way to use the average value of the 100 crystal grains as the average crystal grain size.

Further, there should be no flaws of 10 μm or more from the surface to the depth of 250 μm, and no snow flakes of 20 μm or more.

When there are flaws of 10 μm or more and snow flakes of 20 μm or more, the resistance against the external stress such as shock deteriorates and wear resistance and durability decrease, and, when there are no flaws of 5 μm or more and snow flakes of 10 μm or more, this is more preferable.

The flaws include not only scratches, cracks and air holes, but also aggregation of a sintering agent and a second phase containing impurities.

It is possible to evaluate whether or not there are flaws and snow flakes on the surface and near the surface by allowing transmission of halogen light having the wavelength between 500 nm and 800 nm in the sintered compact, and allow transmission of light from the surface to the depth of 250 μm under observation conditions of the present invention.

Figure 1:
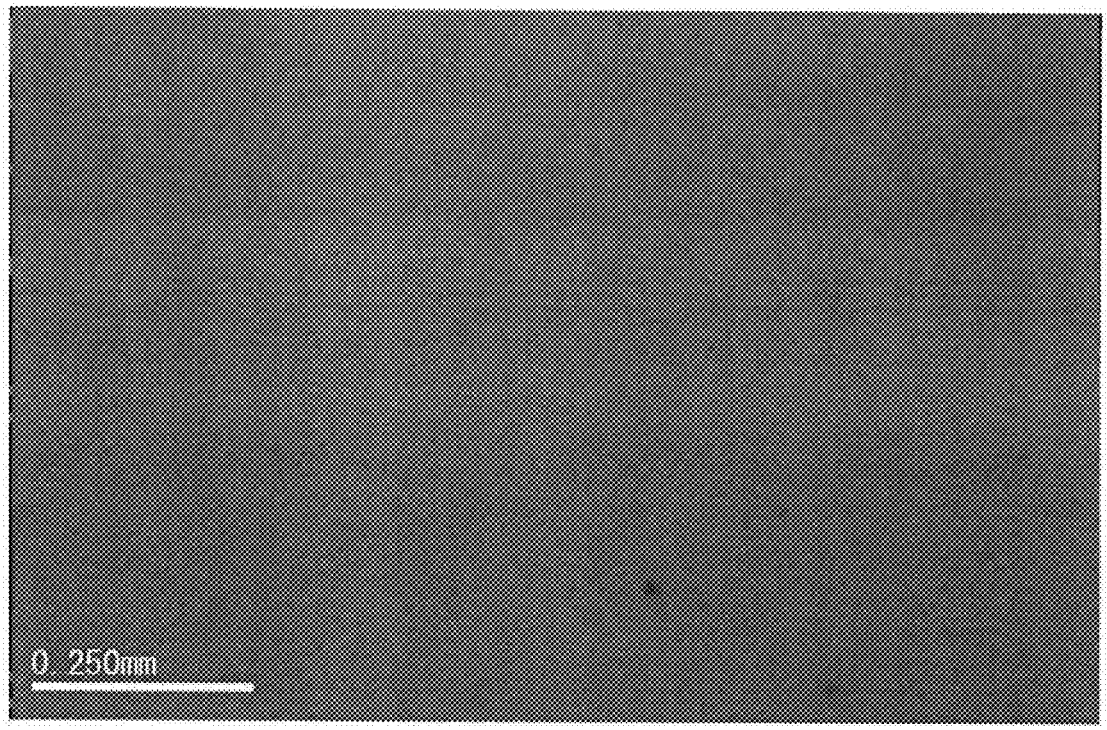
FIG. 1 is a halogen light transmission optical micrograph of a sintered ceramic according to the present invention.
Figure 1:
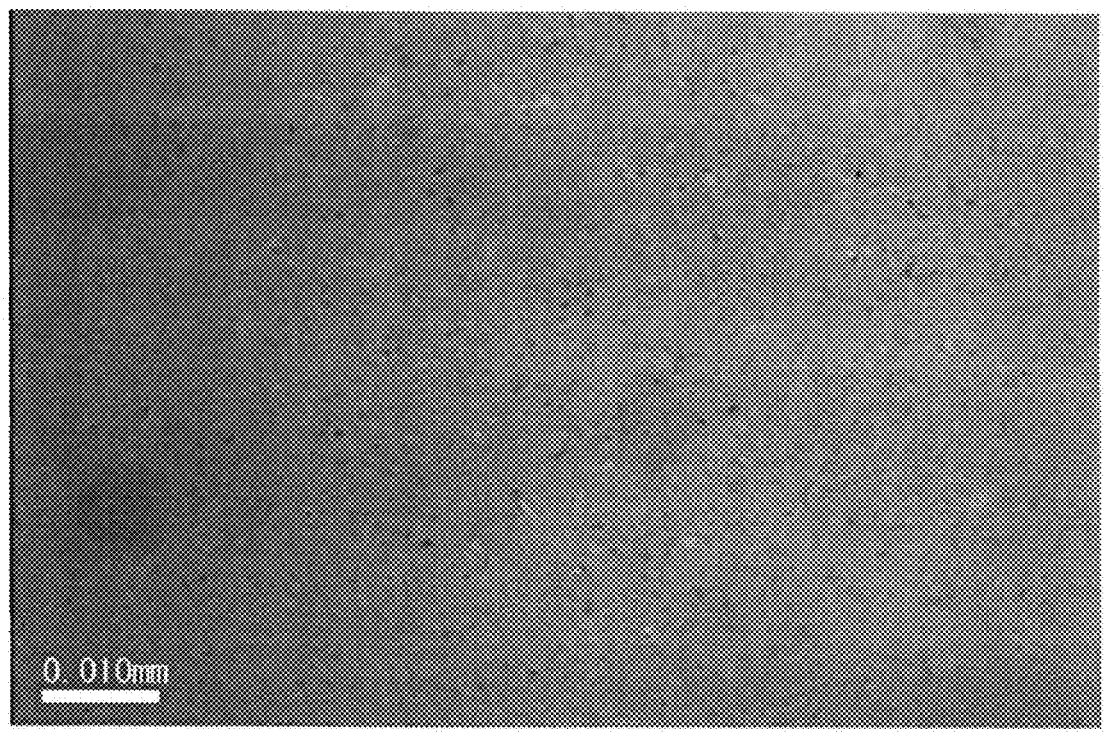
Figure 2:
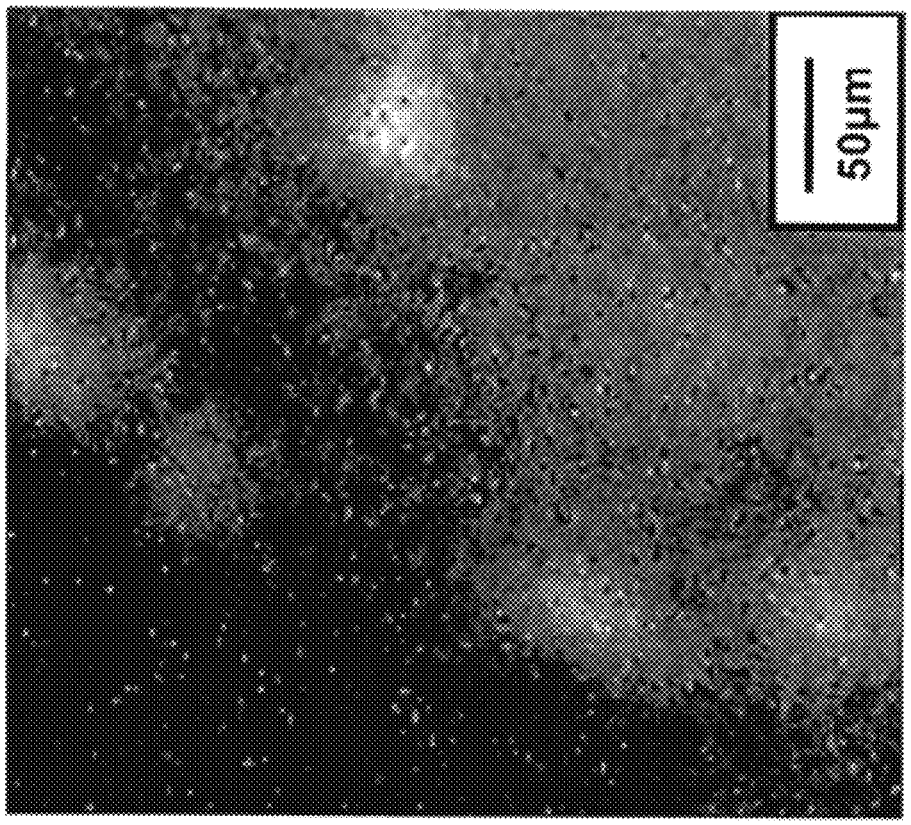
FIG. 2 is a micrograph of a conventional sintered ceramic.
Figure 2:
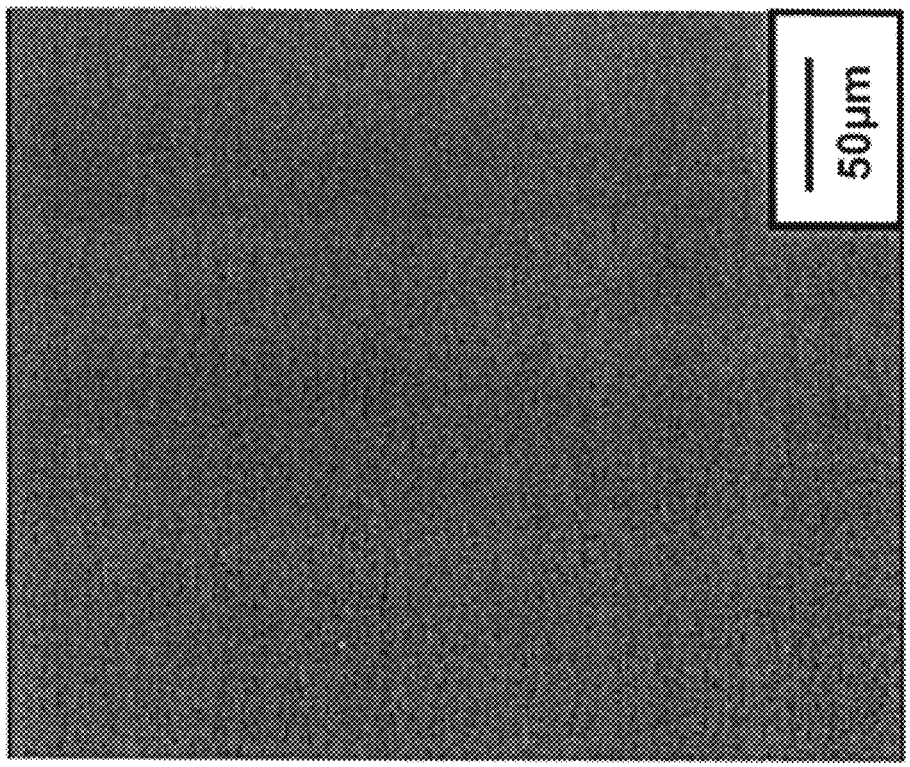

FIG. 1 is an optical micrograph showing that the sintered ceramic according to the present invention is sliced to 0.2 mm of a sheet thickness and polished and halogen light having the wavelength between 500 nm and 800 nm is transmitted, and that no snow flakes and flaws can be observed.

Figure 3:
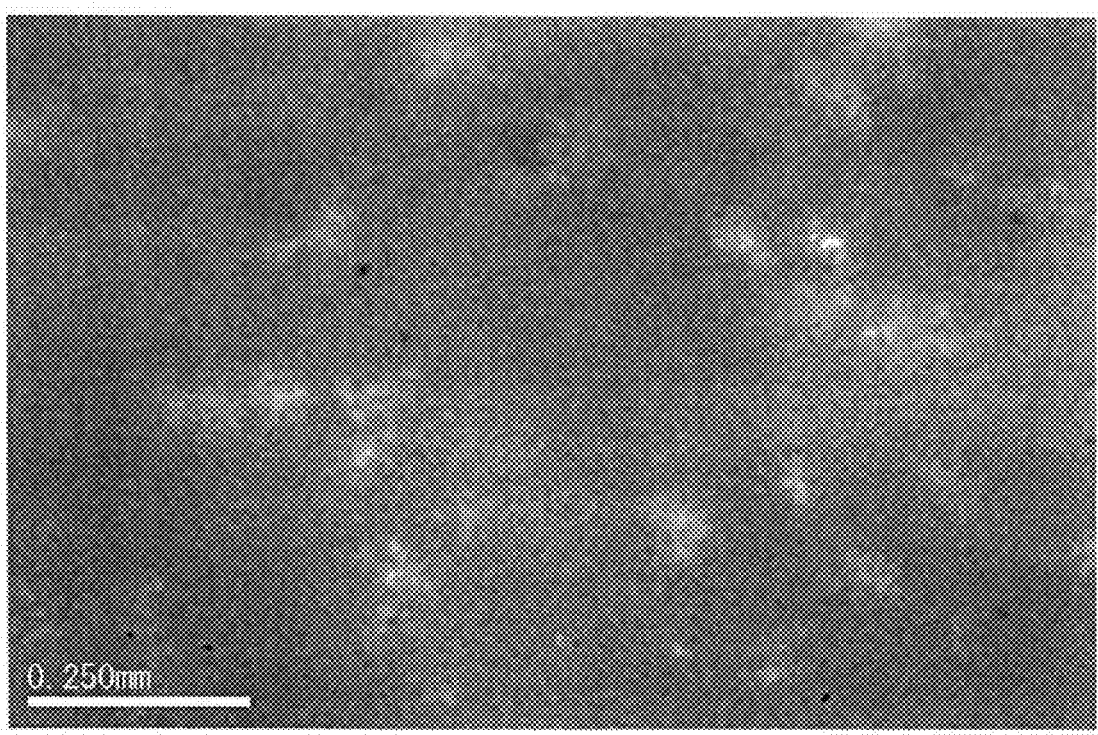
FIG. 3 is a halogen light transmission optical micrograph of a conventional sintered ceramic.
Figure 3:
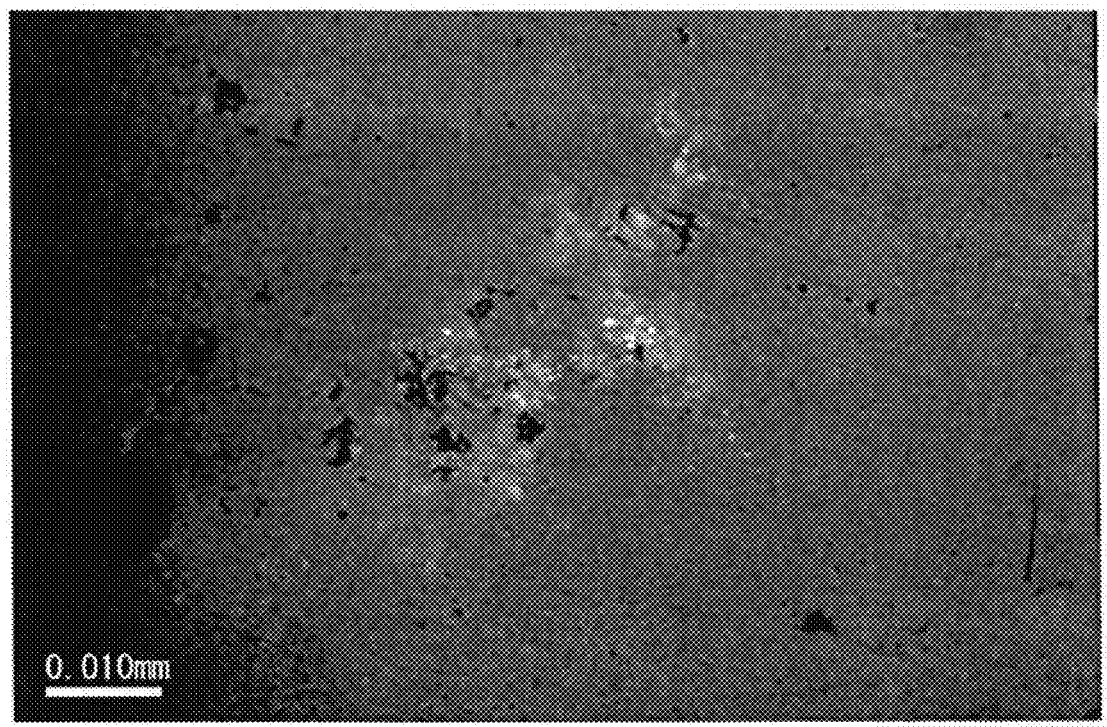

Meanwhile, FIG. 3 is an optical micrograph showing that a conventional sintered ceramic is sliced to 0.2 mm of a sheet thickness and polished and halogen light having the wavelength between 500 nm and 800 nm is transmitted, and that snow flakes and flaws which are supposed to be segregation can be clearly observed.

When light does not transmit from the surface to the depth of 250 μm or when transmission light is uneven, this means that there are not only flaws in portions between the surface and the depth of 250 μm but also snow flakes of at least 20 μm or more.

Therefore, when halogen light does not transmit from the surface to the depth of 250 μm or transmission light is uneven, wear resistance and durability decrease.

In addition, with the present invention, flaws are measured by polishing a sintered compact to have a mirror surface using a diamond wheel and abrasive grains, observing ten sites at random at 1000 folds of the magnification by means of the SEM and using the observed maximum size of the flaws for the flaw size.

Further, snow flakes are measured in a similar manner by observing ten sites at random in the mirror-polished sintered compact at 100 folds of the magnification by means of an optical microscope using halogen light having the wavelength between 500 nm and 800 nm, and using the observed maximum size of the snow flakes as the size of the snow flakes.

The sintered ceramic according to the present invention which has excellent wear resistance has high mechanical characteristics, and, for example, a two-sphere crushing load against a bearing ball of the ⅜ inch standard made of the sintered ceramic according to the present invention and a SUJ2 ball is 100 kN or more and a two-sphere crushing load of the same bearing balls is 20 kN or more.

Further, the sintered ceramic according to the present invention has excellent wear resistance, durability and mechanical characteristics and, consequently, is useful as a rolling bearing member.

Figure 4:
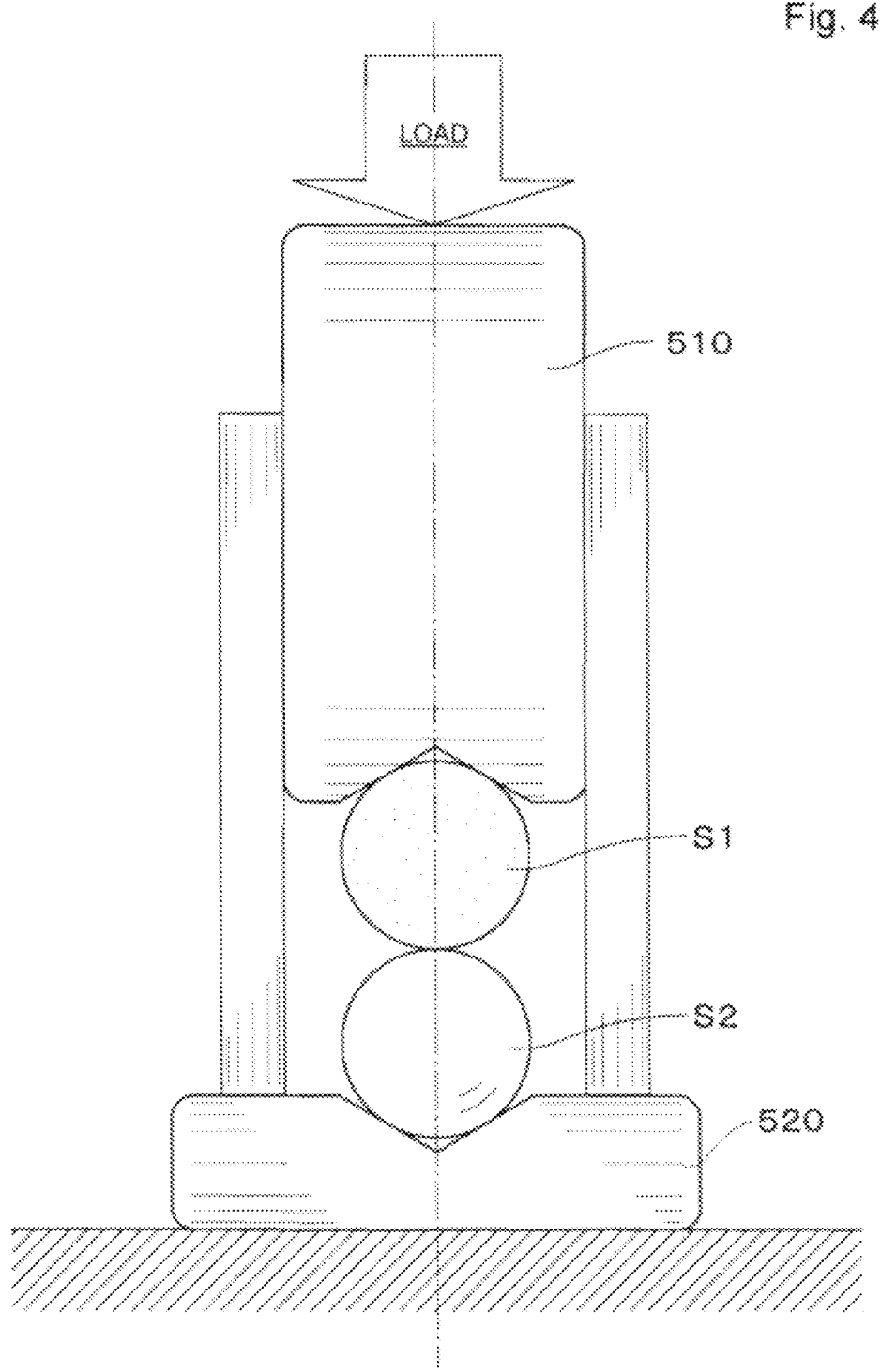
FIG. 4 is an explanatory view of measurement of a crushing load.

In addition, the crushing load is measured by applying the load at a speed of 2 to 6 kN/s (204 to 612 kgf/s) (a method based on previous JISB1501) in a state where two measurement target spheres S1 and S2 of the same size are vertically aligned by anvils 510 and 520 provided above and below S1 and S2 and having hardness of HRC60 or more and conical seats at an angle of 120° C., as shown in FIG. 4.

Measurement performed together with the ceramic sphere and a SUJ2 steel ball is performed by arranging the ceramic sphere above and the SUJ2 steel ball below.

A method of manufacturing the sintered ceramic according to the present invention will be described below.

In addition, the following manufacturing method is an example, and the sintered ceramic and the ceramic sphere according to the present invention are by no means limited by this manufacturing method.

Silicon nitride powder to use includes an a phase of 80% or more and, more preferably, includes the a phase of 90% or more.

The purity needs to be 98% or more and, more preferably, 98.5% or more.

When impurities exceed 2%, multiple phases 2 containing the impurities are formed inside the sintered compact.

The specific surface area is 6 $m^2/g$ or more and, more preferably, 8 $m^2/g$ or more.

When the specific surface area is less than 6 $m^2/g$, sintering performance decreases.

Alumina ($Al_2O_3$) and yttria ($Y_2O_3$) are added as sintering agents with silicon nitride powder having the above characteristics.

By adding the amount of 3 to 6 wt % and, more preferably, 4 to 6 wt % of alumina and yttria, it is possible to not only provide excellent wear resistance but also to provide the composition which allows transmission of halogen of 500 nm to 800 nm.

Alumina to use needs to have the purity of 99% or more and, more preferably, 99.5% or more, and the specific surface area needs to be 6 $m^2/g$ or more and, more preferably, 7 $m^2/g$ or more.

Further, the purity of yttria needs to be 99% or more and, more preferably, 99.5% or more, and the specific surface area needs to be 8 $m^2/g$ or more and, more preferably, 9 $m^2/g$ or more.

When the purities of alumina and yttria powder do not satisfy defined values, the amount of impurities increases similarly to a case where the purity of silicon nitride powder is less than the defined value.

Further, when the specific surface area of powder does not satisfy a defined value, it is hardly diffused evenly in the silicon nitride powder, and an aggregate of sintering agents is formed in the sintered compact and unevenness in the composition of the glass phase increases, thereby producing snow flakes.

A medium agitating mill is preferably used instead of a mill such as a ball mill to mix and evenly diffuse silicon nitride powder, alumina and yttria powder.

Molding powder is obtained by adding a binder of a given amount to the resulting evenly-mixed powder and SD-drying the powder.

The specific surface area of the molding powder is 10 to 15 $m^2/g$ and, more preferably, 10 to 13 $m^2/g$.

While sintering performance is low when the specific surface area of molding powder is less than 10 $m^2/g$, powder becomes fine when the specific surface area exceeds 15 $m^2/g$, molding pressure transmissibility upon molding decreases, multiple flaws are formed inside the compact and multiple flaws are formed inside the sintered compact after sintering.

The molding powder is molded in a given shape using CIP (Cold Isostatic Press) molding to obtain an even compact.

A molding pressure works only in one direction according to a press molding method using a mold, the density difference between an inner part and an external part of the compact becomes significant, and the residual stress is produced in the sintered compact due to a sintering shrinkage difference, thereby producing, for example, cracks and leading to flaws in the compact.

The resulting compact is degreased and is then sintered.

The temperature of heating the compact in a sintering container made of silicon nitride is increased from the room temperature to 1000 to 1250° C. in vacuum of $10^{-2}$ Pa or less, and the compact is then sintered at 1600 to 1850° C. and, more preferably, at 1600 to 1800° C. in a nitrogen atmosphere.

Heating in this vacuum is directed to removing components which negatively influence sintering performance vaporizing from the compact due to heating, and removing a hydroxyl group or oxygen adsorbed to the surface of silicon nitrogen powder due to, for example, raw material processing.

When heating is performed in vacuum at a temperature less than 1000° C., this effect does not work and, when the heating is performed to a temperature more than 1250° C. in vacuum, the discharged amount of, for example, oxygen contained in the compact increases, and, as a result, the amount of the glass phase formed in the sintered compact decreases and flaws such as air holes increase in the crystal grain boundary.

Further, when the sintering temperature is less than 1600° C., sintering is not promoted and, when the sintering temperature exceeds 1850° C., dissolution of silicon nitride is promoted, thereby forming, for example, multiple flaws and decreasing mechanical properties.

In addition, the compact is put in the sintering container made of silicon nitride and sintered.

When a sintering container made of carbon is used, carbon gas is produced at 1500° C. or more and solid-soluted in the compact which is being sintered, the color tone increases, and not only halogen light is not transmitted but also flaws on the surface and near the surface increase and mechanical characteristics decrease.

Further, by performing HIP processing of the resulting sintered compact, it is possible to obtain a high quality sintered compact with little flaws. In addition, HIP processing conditions include that HIP processing is performed at 1500 to 1700° C. and, more preferably, at 1550 to 1700° C. at a gas pressure of 100 MPa or more.

Although the resulting sintered ceramic is processed to a given size to make a wear resistant member, the sintered ceramic according to the present invention includes no flaws and no snow flakes, so that it is possible to increase process accuracy and surface roughness.

Consequently, when the ceramic sphere is used as a bearing ball, it is easy to make the sphericity of 0.05 µm or less and surface roughness (Rmax) of 0.01 µm or less.

As examples and comparative examples according to the present invention, a sintered ceramic was sintered under each condition illustrated in FIG. 5 to make a bearing ball of the ⅜ inch standard.

These bearing balls were made by wet pulverizing and mixing silicon nitride powder, alumina and yttria powder, adding wax emulsion of 3% by weight of the powder weight to the resulting mixed slurry, performing spray-drying and performing CIP molding at the pressure of 100 MPa using a rubber mold.

Further, the resulting compact was degreased at 400° C. in the atmosphere, put in the sintering container made of silicon nitride, heated in vacuum of $10^{-2}$ Pa from the room temperature to 1100° C. and sintered for four hours at 1560 to 1880° C. in the nitrogen atmosphere to make a ball of φ10 mm.

In addition, in Comparative Example 3, the compact was heated in vacuum of $<10^{-2}$ Pa from the room temperature to 1350° C. and was sintered and, in Comparative Example 2, the compact was heated in vacuum of <10⁻² Pa from the room temperature to 800° C. and was sintered.

Further, in Comparative Example 9, the compact was sintered using the sintering container made of carbon upon sintering.

The balls made were polished and processed to make bearing balls of the ⅜ inch standard.

FIG. 6 illustrates characteristics and results of fine structure observation and endurance of these bearing balls.

In addition, the endurance test was conducted by embedding a bearing ball in Brg6206 (9/Brg), and using a Gakushin-type life tester (pure rolling) at 2000 rpm of the number of primary axis rotations with 850 kgf of a load (pure radial load) and using clean oil (60° C.) for smoothness, and, if rotation continued for 1300 h without abnormality, the test was finished.

FIG. 7 illustrates two-sphere crushing load test results of bearing balls of the ⅜ inch standard made of the sintered ceramic according to one embodiment of the present invention obtained as described above.

Samples used for experiments include samples illustrated in FIGS. 5 and 6 according to Example 5 of the present invention and examples illustrated in FIGS. 5 and 6 according to Comparative examples 4 and 6, and the samples of the same manufacturing lot are used for examples and comparison examples.

Further, the speed to add a crushing load was 6 kN/s (612 kgf/s).

Although, with the bearing ball according to Comparative Example 4, upon two-sphere crushing of two bearing balls, a crushing load is roughly 20 kN or more and the crushing strength is good and stable, upon two-sphere crushing against a steel ball (SUJ-2 ball), a crushing load is 67.7 to 115.7 kN, the crushing strength significantly varies including a low strength and characteristics are not stable.

While, with the bearing ball according to Comparative Example 6, upon two-sphere crushing against a steel ball (SUJ-2 ball), a crushing load is 78.5 to 112.8 kN and has variation less than in Conventional Example 1 and varies including a little crushing strength, and, even upon two-sphere crushing of bearing balls, the crushing load is 13.7 to 19.2 kN, the crushing strength is low and varies, and characteristics are not stable.

With the bearing balls according to Comparative Examples 4 and 6, snow flakes in the bearing balls make an irregular inner stress state uneven and become a starting point of destruction, internal distortion remains, the amount of an agent exceeding a given amount and a sintering temperature higher than a given temperature increases a thermal expansion difference between silicon nitride crystal and the glass phase and increases internal distortion, and unevenness in the composition increases. Therefore it is not possible to stably secure the crushing strength and it is difficult to make characteristics of multiple bearing balls even.

In contrast, with the bearing ball according to Example 5, upon two-sphere crushing of bearing balls, the crushing load is 20 kN or more and, even upon two-sphere crushing against a steel ball (SUJ-2 ball), the crushing load is 100 kN or more, and both of crushing strengths are good and vary little, and characteristics are stable.

With the bearing ball according to Example 5, there are no snow flakes observed by the optical microscope, in the bearing ball and, for example, no distortion remains inside, so that it is possible to stably secure the crushing strength and make characteristics of multiple bearing balls even.

Further, FIG. 8 illustrates dimensional accuracy measurement results of a bearing ball of a ⁵⁄₃₂ inch standard.

Samples used for experiments include samples illustrated in FIGS. 5 and 6 according to Example 5 of the present invention and examples illustrated in FIGS. 5 and 6 according to Comparative Example 4, and ten samples of the same manufacturing lot are extracted at random and used for examples and comparison examples.

The bearing balls according to Example 5 and Comparative Example 4 are finally polished and processed such that the sphericity is 0.03 μm, and both of the bearing balls are finished with substantially stable accuracy in the range of 0.02 μm to 0.04 μm.

With this sample, the bearing ball according to Comparative Example 4 has significantly varying surface roughness (Rmax) of 0.0053 to 0.0127 μm, and has unstable accuracy.

With the bearing ball according to Comparative Example 4, irregular snow flakes in the surface layer of the sintered ceramic make wear resistance different from other portions, make the amount of agent greater than a given amount, increases a thermal expansion difference between silicon nitride crystal and the glass phase, increases inner distortion and increases unevenness in the composition, thereby preventing improvement in surface roughness upon polishing and processing and making it difficult to make surface roughness of multiple bearing balls even.

In contrast, the bearing ball according to Example 5 has good surface roughness (Rmax) of 0.0040 to 0.0077 μm and little variation, and has stable accuracy.

With the bearing ball according to Example 5, there are no snow flakes observed by the optical microscope, and wear resistance of the surface is even, so that it is possible to improve surface roughness upon polishing and processing and make surface roughness of multiple bearing balls even.

By employing the bearing ball using the sintered ceramic according to the present invention having the above characteristics, for a rolling member of a sliding device such as a bearing or a ball nut or a valve and the like of fluidic valve which controls a high pressure fluid, it is possible to reduce the weight of a sliding device and a fluidic valve, prevent damages due to a load and repetitions of sliding or damages and the like by wear, corrosion and electrical corrosion, maintain performance for a long period of time, increase the life of components of the sliding device and the fluidic valve and reduce maintenance labor, which are effects originally derived from characteristics of the sintered ceramic. In addition, it is possible to reduce surface peeling due to fatigue resulting from repetitions of loading, stably provide multiple products after removing variations in, for example, characteristics and accuracy according to lot and variations in, for example, characteristics and accuracy of individual bearing balls of the same lot and reduce the manufacturing time and manufacturing cost, and consequently, it is possible to stably make performance higher and a life longer, reduce maintenance labor and reduce cost.

Further, dimensional accuracy such as the sphericity and surface roughness of the bearing ball improves, so that it is possible to suppress wear, vibration and noise and cancel an influence on the entire mechanical device of use due to wear and vibration.

In addition, although the sintered ceramic according to the above example is formed in a spherical shape and processed to a bearing ball, the sintered ceramic may be formed in any shape such as a roller shape including, for example, a columnar shape, a circular truncated conical shape, a barrel shape or a hourglass shape other than the spherical shape, or a race shape of a bearing, and may be used in any components of any devices for which the sintered ceramic can be used.

Example 1

Next, a ceramic-sphere inspection device according to the present invention will be described.

Figure 9:
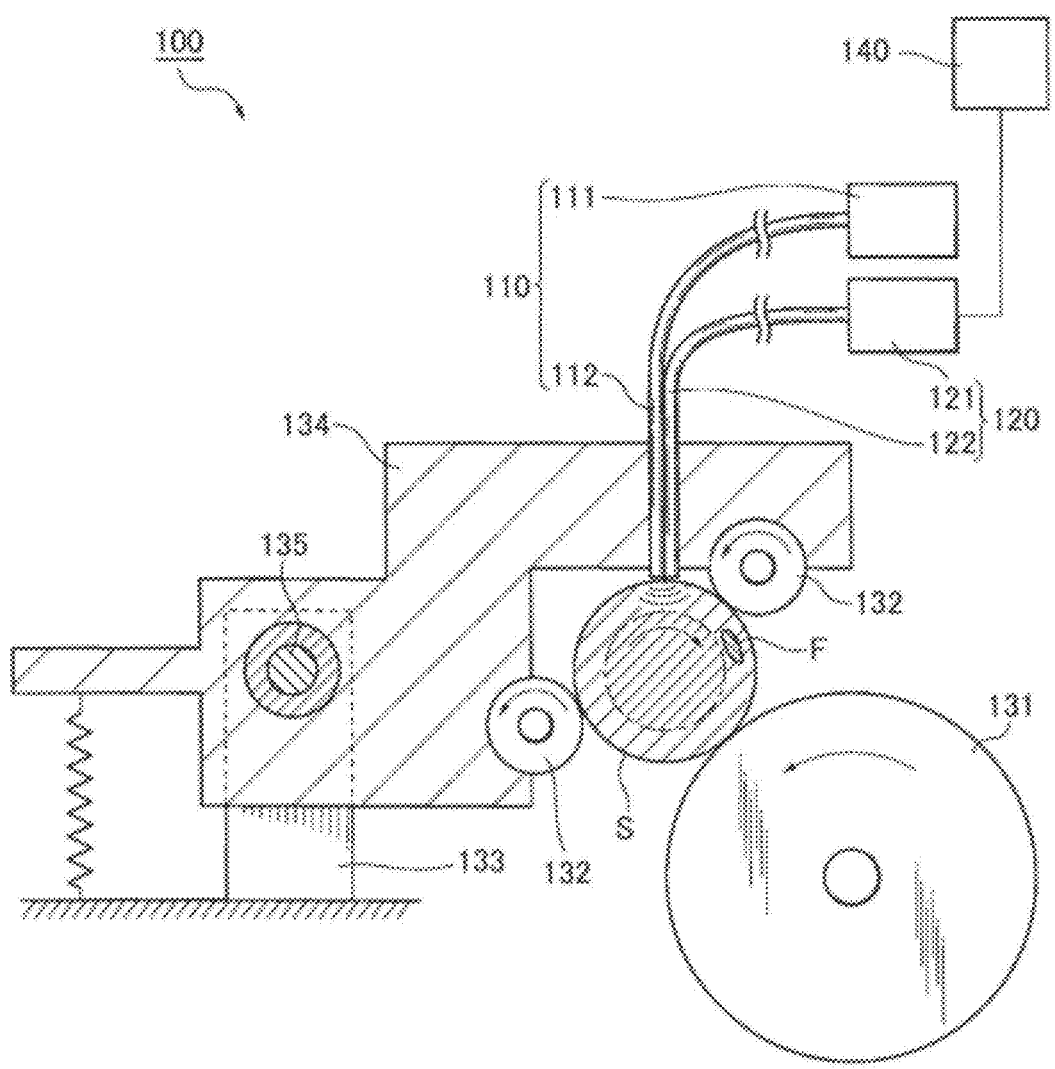
FIG. 9 is a schematic side view of a ceramic-sphere inspection device according to a first example of the present invention.
Figure 10:
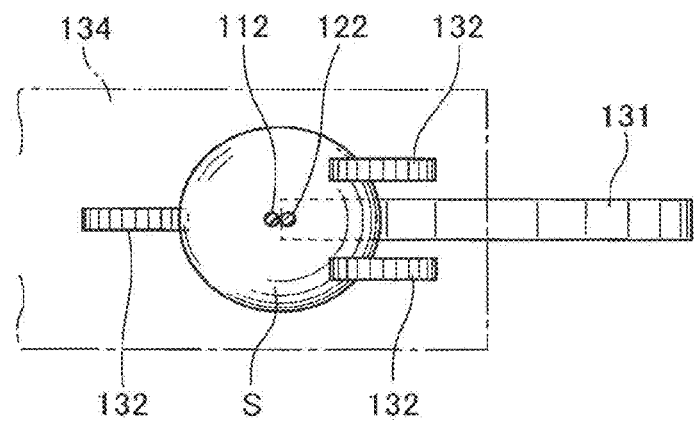
FIG. 10 is a schematic plan view of the ceramic-sphere inspection device according to the first example of the present invention.

As illustrated in FIGS. 9 and 10, a ceramic-sphere inspection device 100 according to an example 1 of the present invention has a rotation supporter which rotatably supports a ceramic sphere S, which is an inspection target, at a given position, a light projector 110 which emits illuminating light toward the surface of the ceramic sphere S, a light receiver 120 which detects light reflected from the ceramic sphere S as inspection light and a processor 140 which evaluates a state of an inner part of the surface layer of the ceramic sphere S in response to a detection output from the light receiver 120.

The rotation supporter is formed with one driving roller 131 and a plurality of driven rollers 132, and the plurality of driven rollers 132 are pivotally supported by a holding member 132 rotatably.

The holding member 134 is supported by a swing supporting unit 133 to swing about a swing shaft 135, so that the ceramic sphere S is rotatably held between one driving roller 131 and the plurality of driven rollers 132 and the held ceramic sphere S can be released.

The light projector 110 has a light source 111, and a light projecting unit 112 which guides light of the light source 111 as illuminating light to a surface of the ceramic sphere S.

The light receiver 120 has a light amount detecting unit 121 and a light receiving unit 122 which guides inspection light from the ceramic sphere S to the light amount detecting unit 121.

Front ends of the light projecting unit 112 and the light receiving unit 122 form contact surfaces which can contact the surface of the ceramic sphere S, and are held by a proceeding/retreating mechanism, which is not illustrated, in the holding member 134 to proceed and retreat to and from the surface direction of the ceramic sphere S.

The light source 111 only needs to include a wavelength which allows illuminating light to transmit to the inner part of the surface layer and include the amount of light which is irregularly diffused and spreads in the inner part and reaches the light receiving unit 122, and may be any light source such as a laser light source which can efficiently output only an optimal wavelength or a halogen light source which is cheap and has a great amount of light.

When, for example, whether or not there are flaws and snow flakes on the surface and near the surface is observed, the sintered ceramic according to the present invention allows transmission of halogen light up to about 250 μm, and light having a wavelength between 500 nm and 800 nm can be observed, so that it is possible to employ, for example, a common halogen light source without providing a costly light source such as laser or a complicated optical system and the like.

Further, the light projecting unit 112 and the light receiving unit 122 only need to block light from surfaces other than the contact surfaces, and may use, for example, optical fibers and the like.

The driving roller 131 can be intermittently driven, the contact surfaces at the front ends of the light projecting unit 112 and the light receiving unit 122 repeat closely attaching to the surface of the ceramic surface S when driving of the driving roller 131 is stopped to optically observe the inner part of the surface layer and detaching from the surface of the ceramic sphere S when the driving roller 131 is driven.

According to the above configuration, at multiple portions on the surface of the ceramic sphere S, it is possible to observe only illuminating light transmitted and diffused in the inner part of the surface layer and reflected from the inner part without detecting the light reflected from the surface.

Consequently, it is possible to accurately detect flaws in the inner part of the surface layer and snow flakes F formed based on a slight difference in the composition of a crystal grain boundary phase, as a change of inspection light detected by the light receiver without destroying the ceramic sphere and depending on the surface state, and inspect whether the material of the ceramic sphere is good and the ceramic sphere is sintered well by observing the total amount of inspection light.

In addition, although, with the present example, the light projecting unit 112 and the light receiving unit 122 are integrated and held by the holding member 134 to proceed and retreat to and from the surface direction of the ceramic surface S, only one of the light projecting unit 112 and the light receiving unit 122 may be held to proceed and retreat and the light projecting unit 112, and the light receiving unit 122 may be fixed in a state where both of them are in contact with the surface of the ceramic sphere S.

Further, as long as the distance between the front ends of the light receiving unit 112 and the light receiving unit 122 is separated such that light reflected from the surface is not detected, both of the light projecting unit 112 and the light receiving unit 122 may be fixed at a position at which both of them do not contact the surface of the ceramic sphere S.

When both of the light projecting unit 112 and the light receiving unit 122 are fixed, the driving roller 131 may be continuously driven instead of being intermittently driven.

Further, the ceramic-sphere inspection device 100 is not only applicable to the ceramic sphere according to the present invention and any ceramic sphere as long as ceramic spheres are made of materials which allow transmission of illuminating light to the inner part of the surface layer such as silicon nitride sintered compact made according to other compositions or other manufacturing methods and ceramics mainly made of, for example, alumina, zirconia and sialon.

When, for example, a halogen light source emits light, materials are known which allow transmission of light to about 3 to 8 mm in case of alumina and transmission of light to about 2 to 3 mm in case of zirconia, and these materials can be inspected.

Second Example

Next, an example will be described where a configuration is employed for observing the entire surface of the ceramic sphere all over.

With the ceramic-sphere inspection device 200 according to Example 2 of the present invention, a rotation supporter is formed with one driving roller 231 and a plurality of driven rollers 232 similarly to Example 1, and the plurality of driven rollers 232 is pivotally and rotatably supported by a holding member 234.

Figure 11:
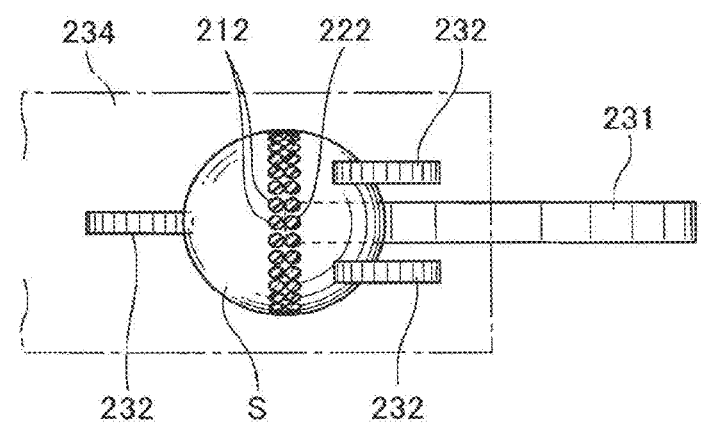
FIG. 11 is a schematic plan view of a ceramic-sphere inspection device according to a second example of the present invention.
Figure 12:
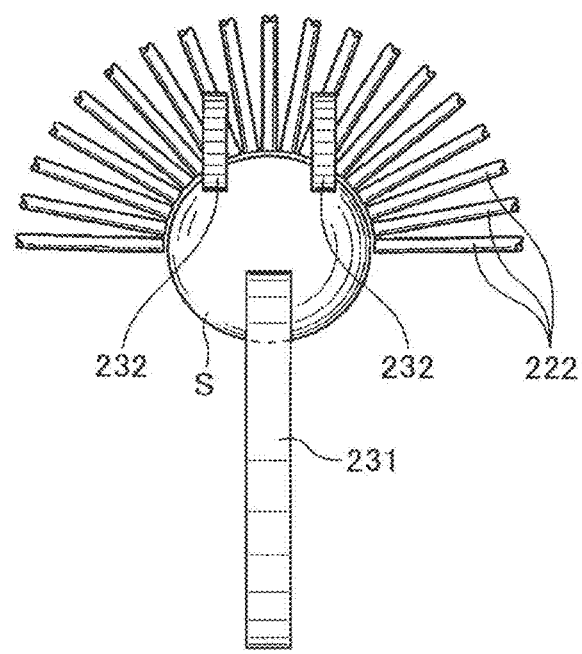
FIG. 12 is a schematic front view of the ceramic-sphere inspection device according to the second example of the present invention.

Further, as illustrated in FIGS. 11 and 12, a plurality of light projecting units 212 and light receiving units 222 are provided over a semicircle of an outer peripheral circle in the cross section passing the center of the ceramic sphere and at a right angle with respect to the rotation direction.

Consequently, by rotating the ceramic sphere S once, it is possible to observe the entire surface and efficiently inspect the ceramic sphere S.

In addition, although the projecting units 212 and the light receiving units 222 are drawn bold for ease of understanding, a greater number of the projecting units 212 and the light receiving units 222 can be provided using thin components such as optical fibers more than the illustration.

Further, the number of light projecting units 212 may be less than the number of light receiving units 222.

Example 3

Figure 13:
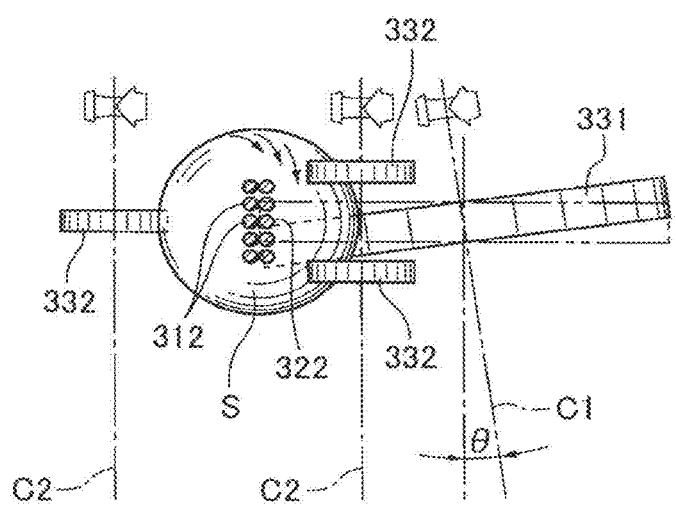
FIG. 13 is a schematic plan view of a ceramic-sphere inspection device according to a third example of the present invention.

As illustrated in FIG. 13, with, a ceramic-sphere inspection device 300 according to Example 3 of the present invention, a rotation supporter is formed with one driving roller 331 and a plurality of driven rollers 332, and the plurality of driven rollers 332 are pivotally supported by a holding member 334 to rotate around parallel rotation shaft lines C2 and the driving roller 331 is rotatable around a rotation shaft line C1 inclined at a given angle θ from the rotation shaft lines C2 of the plurality of driven rollers 332.

Further, a plurality of light projecting units 312 and light receiving units 322 are provided along an outer peripheral circle in the cross section passing the center of the ceramic sphere S and at a right angle with respect to the rotation direction.

The inclination angle θ of the rotation shaft line C1 of the driving roller 331 is set to be shifted by the width of the plurality of light receiving units 322 when the ceramic sphere S rotates around.

Although it is necessary to rotate the ceramic sphere S a plurality of times to observe the entire surface, it is possible to observe the entire surface using a less number of light receiving units 322 than in Example 2.

In addition, although the light projecting units 312 and the light receiving units 322 are drawn bold for ease of understanding similarly to Example 2, a greater number of the projecting units 312 and the light receiving units 322 can be provided using thin components such as optical fibers more than the illustration.

Further, the number of light projecting units 312 may be less than the number of light receiving units 322.

Figure 14:
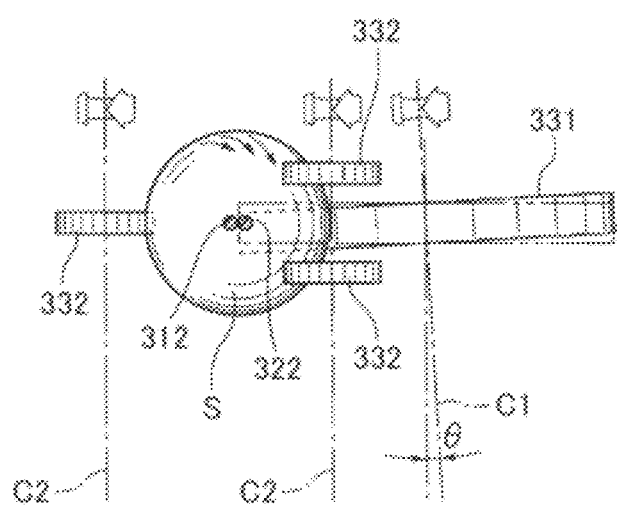
FIG. 14 is a schematic plan view of another embodiment of the ceramic-sphere inspection device according to the third example of the present invention.

Further, as illustrated in FIG. 14, the number of the light receiving unit 312 and the number of the light receiving unit 322 may be one, respectively, so that the inclination angle θ of the rotation shaft line C1 of the driving roller 331 becomes slight.

Consequently, an operation of adjusting the light amount and the sensitivity of a plurality of light projecting units and light receiving units is not required at all, so that it is easy to maintain inspection accuracy.

In addition, the rotation supporter is by no means limited to the above examples and may employ any configuration as long as it supports the ceramic sphere S rotatably at a given position according to the same operation as in Examples 1 to 3.

Figure 15:
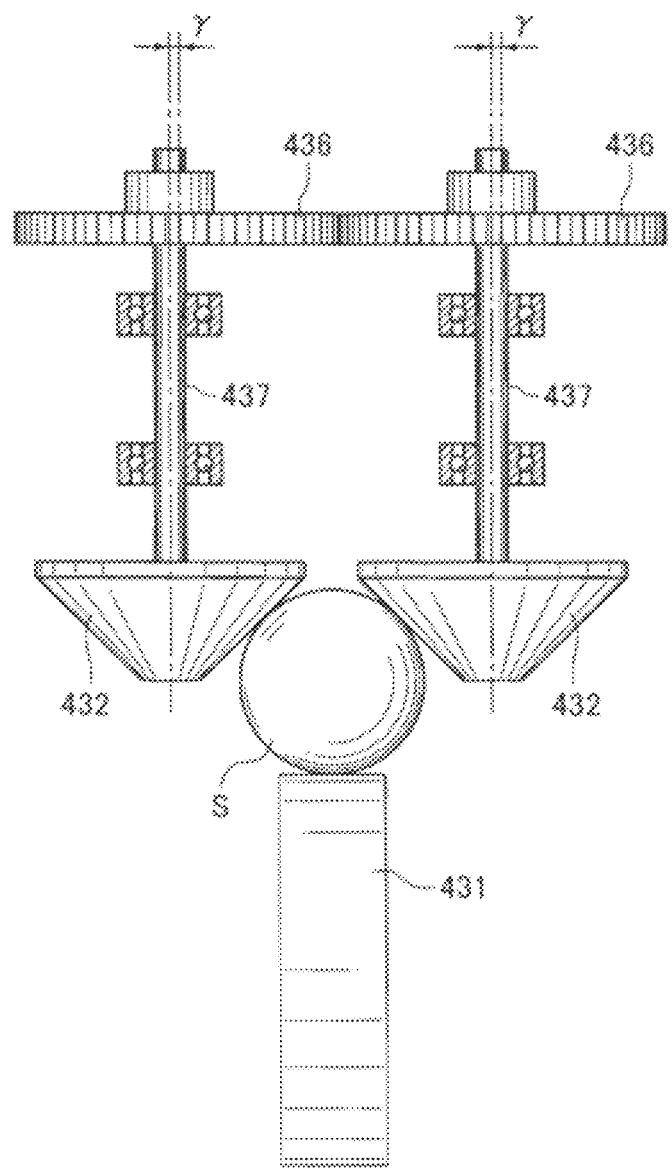
FIG. 15 is a schematic view of another embodiment of the ceramic-sphere inspection device according to the present invention.

For example, as illustrated in FIG. 15, two opposing driven rollers 432 which rotatably support the ceramic sphere S may have conical trapezoidal shapes having rotation shafts 437 extending in a longitudinal direction. According to this configuration, by decentering gears 436 by a decentering amount r to attach to the rotation shafts 437 of the two opposing driven rollers 432 and cyclically fluctuating rotation speeds of the two driven rollers 432, it is possible to rotate the ceramic sphere S, and observe the entire surface of the ceramic sphere S all over with twisting movement.

Further, as illustrated in FIG. 16, driving rollers 531 are formed in shaft shapes having parallel grooves 538 and screw grooves 539 to continuously inspect a plurality of ceramic spheres S.

With the embodiment illustrated in FIG. 9, a plurality of parallel grooves 538 extending in a circumferential direction over about a semicircle of the shaft-shaped driving rollers 531, and a plurality of screw grooves 539 extending to connect to the parallel grooves 538 adjacent in the other semicircle continuing to the parallel grooves 538 are formed.

Further, light receiving units 522 are provided to meet the parallel grooves 538, respectively, and the ceramic spheres S are rotated in the parallel grooves 538 at the position of the light receiving units 522, and moved by the screw grooves 539 in the shaft direction of the driving roller 531 to change the rotation shaft.

By this means, the ceramic spheres S are continuously introduced from the left direction in FIG. 16, are carried to the parallel grooves 538 sequentially in the right direction, and are observed while the rotation shafts are sequentially changed by the light receiving units 522 meeting the parallel grooves 538 respectively to continuously observe the entire spherical surface.

In addition, as illustrated in FIGS. 15 and 16, in another embodiment of a rotation supporter, the numbers of light receiving units and light projecting units may be one or plural, and, further, the driving roller may be intermittently driven, and the light receiving units and the light projecting units may proceed and retreat to and from the surface direction of the ceramic spheres S and closely attach to the surfaces of the ceramic spheres S only when the driving roller stops.

REFERENCE SIGNS LIST 100, 200, 300 CERAMIC-SPHERE INSPECTION DEVICE
110 LIGHT PROJECTOR
111 HALOGEN LIGHT SOURCE
112, 212, 312 LIGHT PROJECTING UNIT
120 LIGHT RECEIVER
121 LIGHT AMOUNT DETECTING UNIT
122, 222, 322, 522 LIGHT RECEIVING UNIT
131, 231, 331, 431, 531 DRIVING ROLLER
132, 232, 332, 432 DRIVEN ROLLER
133 SWING SUPPORTING UNIT
134 HOLDING MEMBER
135 SWING SHAFT
436 GEAR
437 ROTATION SHAFT
538 PARALLEL GROOVE
539 SCREW GROOVE
S CERAMIC SPHERE
F SNOW FLAKE F
S1, S2 MEASUREMENT TARGET SPHERE
510, 520 ANVIL

The invention claimed is:

1. A sintered ceramic which has excellent wear resistance and which is obtained by molding and sintering a molding powder with a specific surface area of 10 to 15 m$^2$/g, the powder comprising silicon nitride and a sintering agent made of $Al_2O_3$ and $Y_2O_3$, each of which is added at 3 to 6 wt %, wherein a bulk density is 3.1 g/cm³ or more, an average grain size is 3 μm or less, and there are no flaw of 10 μm or more from a surface to a depth of 250 μm and no white spot (snow flake) of 20 μm or more when mirror-polishing a silicon nitride sintered compact and allowing transmission of halogen light having the wavelength between 500 nm and 800 nm therein.

2. A ceramic sphere which has excellent wear resistance and which is obtained by molding and sintering a molding powder with a specific surface area of 10 m²/g to 15 m²/g, the powder comprising silicon nitride and a sintering agent made of $Al_2O_3$ and $Y_2O_3$, each of which is added at 3 wt % to 6 wt %, wherein a bulk density is 3.1 g/cm³ or more, an average grain size is 3 μm or less, and there are no flaw of 10 μm or more from a surface to a depth of 250 μm and no white spot (snow flake) of 20 μm or more when mirror-polishing a silicon nitride sintered compact and allowing transmission of halogen light having the wavelength between 500 nm and 800 nm therein.

3. A wear resistant member formed using a sintered ceramic, wherein a surface of the sintered ceramic according to claim 1 is processed to make a rolling bearing member.

\* \* \* \* \*